(12) United States Patent
van Dommelen

(10) Patent No.: US 11,175,162 B2
(45) Date of Patent: Nov. 16, 2021

(54) INTEGRATED CIRCUIT SENSOR PACKAGE AND METHOD OF MANUFACTURING THE SAME

(71) Applicant: Sencio B.V., Nijmegen (NL)

(72) Inventor: Ignatius Josephus van Dommelen, Vorstenbosch (NL)

(73) Assignee: Sencio B.V., Nijmegen (NL)

( * ) Notice: Subject to any disclaimer, the term of this patent is extended or adjusted under 35 U.S.C. 154(b) by 48 days.

(21) Appl. No.: 16/464,279

(22) PCT Filed: Nov. 29, 2017

(86) PCT No.: PCT/NL2017/050793
§ 371 (c)(1),
(2) Date: May 27, 2019

(87) PCT Pub. No.: WO2018/101821
PCT Pub. Date: Jun. 7, 2018

(65) Prior Publication Data
US 2020/0284624 A1    Sep. 10, 2020

(30) Foreign Application Priority Data
Nov. 29, 2016    (NL) ..................................... 2017885

(51) Int. Cl.
*G01N 33/00*    (2006.01)
*G01D 11/24*    (2006.01)

(52) U.S. Cl.
CPC ....... *G01D 11/245* (2013.01); *G01N 33/0009* (2013.01)

(58) Field of Classification Search
CPC .................. G01D 11/245; G01N 33/0009
See application file for complete search history.

(56) References Cited

U.S. PATENT DOCUMENTS

| | | | |
|---|---|---|---|
| 5,773,323 A * | 6/1998 | Hur | H01L 31/02005 438/123 |
| 6,461,890 B1 * | 10/2002 | Shibata | H01L 24/27 257/E21.514 |
| 9,909,946 B2 * | 3/2018 | Ihle | C04B 35/64 |
| 10,192,842 B2 * | 1/2019 | Bouman | H01L 24/32 |
| 2007/0222008 A1 * | 9/2007 | Chen | B81C 1/00896 257/415 |

(Continued)

FOREIGN PATENT DOCUMENTS

| | | |
|---|---|---|
| CN | 201438461 U | 4/2010 |
| CN | 102346162 A | 2/2012 |

(Continued)

*Primary Examiner* — Jamel E Williams
(74) *Attorney, Agent, or Firm* — N.V. Nederlandsch Octrooibureau; Catherine A. Shultz; Katelyn J. Bernier

(57) ABSTRACT

An integrated circuit sensor package (1) with a package body (5) moulded at least in part around a substrate (2) and a plurality of lead frame members (6, 8). The substrate (2) has a first sensor element (3) on a first side surface (2a). The package body (5) comprises an aperture (5a) exposing a sensitive surface (4) of the first sensor element (3). Electrically conductive glue connections (7, 9) are provided between contact terminals of the first sensor element (3) and one or more of the plurality of lead frame members (6, 8).

14 Claims, 4 Drawing Sheets

(56) References Cited

U.S. PATENT DOCUMENTS

| | | | | |
|---|---|---|---|---|
| 2009/0133474 A1* | 5/2009 | Ng | ................... | B82Y 15/00 |
| | | | | 73/31.06 |
| 2010/0192689 A1* | 8/2010 | Ulm | ................... | G01C 19/56 |
| | | | | 73/430 |
| 2010/0242605 A1* | 9/2010 | Offterdinger | ........... | G01P 1/023 |
| | | | | 73/514.38 |
| 2011/0221303 A1* | 9/2011 | Chiba | ................... | H03H 9/1021 |
| | | | | 310/313 R |
| 2013/0305822 A1* | 11/2013 | Graf | ................... | G01N 27/048 |
| | | | | 73/431 |
| 2014/0184263 A1* | 7/2014 | Ehrenpfordt | ....... | G01R 31/2884 |
| | | | | 324/762.03 |
| 2015/0177171 A1* | 6/2015 | Kim | ................... | G01N 27/128 |
| | | | | 73/31.05 |
| 2015/0226585 A1* | 8/2015 | Yang | ................... | G01D 11/245 |
| | | | | 73/431 |
| 2016/0011020 A1* | 1/2016 | Ehrenpfordt | .......... | H01L 25/167 |
| | | | | 73/431 |
| 2016/0139071 A1* | 5/2016 | Nakano | ................... | G01F 1/684 |
| | | | | 73/23.31 |
| 2020/0132520 A1* | 4/2020 | Katsuhara | ................ | H05K 1/02 |

FOREIGN PATENT DOCUMENTS

| | | | | |
|---|---|---|---|---|
| DE | 102004031318 A1 * | 1/2006 | ....... | H01L 23/49861 |
| EP | 2 315 011 A1 | 4/2011 | | |
| JP | 2006125916 A * | 5/2006 | | |

\* cited by examiner

INTEGRATED CIRCUIT SENSOR PACKAGE AND METHOD OF MANUFACTURING THE SAME

FIELD OF THE INVENTION

The present invention relates to a sensor package, in particular to an integrated circuit sensor package comprising a package body moulded at least in part around a substrate and a plurality of lead frame members. In a further aspect, the present invention relates to a method of manufacturing such an integrated circuit sensor package, wherein the method comprises providing a lead frame of electrically conductive material, the lead frame comprising a plurality of lead frame members.

BACKGROUND

US patent US20150177171A1 discloses a gas sensor package comprising a gas sensor adhered to one side of a readout integrated circuit (IC) device wherein the IC device is electrically connected with a lead frame with bonding wires. The gas sensor comprises a sensing surface on an exposed side, and a heater element on the other side. A micro electro mechanical system (MEMS) based cap including a supporting part and plate are in contact with a mould which is used to cover the readout IC and the lead frame to form the gas sensor package.

European patent publication EP-A-2 315 011 discloses a gas sensor including a plurality of electrode pins which are electrically connected to a gas-sensitive element, and to lead-out leads allowing connections external to the gas sensor assembly. The gas sensor assembly comprises cover members 3, 4, 6 made of porous ceramics to allow gasses from the environment to reach the gas-sensitive element.

German patent publication DE-A-10 2008 015709 discloses an assembly of a sensor chip and a structure supporting the sensor chip and a semiconductor chip. The sensor chip is enclosed by a structure or covering made of formed mass of ceramic or glass material. The sensor chip is e.g. a motion sensor.

SUMMARY

The present invention seeks to provide a sensor package for a sensor requiring (partial) exposure to the environment, such as a gas sensor. Furthermore, the present invention seeks to provide a structure of the sensor package which allows easy, cost effective and reliable manufacturing.

According to the present invention, a sensor package of the type defined in the preamble is provided, wherein the substrate comprises a first sensor element on a first surface of the substrate, wherein the package body comprises an aperture exposing a sensitive surface of the first sensor element, and wherein the integrated circuit sensor package further comprises an electrically conductive glue connection between contact terminals of the first sensor element and one or more of the plurality of lead frame members. Such a glue (or adhesive) based electrically conducting connection between the sensor element and (one or more) lead frame members provides a very reliable electrical connection for a large variety of different types of sensor elements, which is fully compatible with the moulding technique of the sensor package.

An encapsulation technology which is known as such is used for an exposed die type of moulding of the sensor package in order to make sure that the sensitive surface of the sensor element is sufficiently exposed. The sensor package body comprises an aperture exposing at least part of the first sensor element allowing a well-defined area of the sensor fully exposed to the environment properly allowing measurement of the associated sensing parameter. This is specifically relevant for industrial applications such as environmental sensing, gas sensing, flow sensing and for bio-sensing. Due to the fact that sensors are getting smaller in size, the present invention enables cost-effective manufacturing of advanced functional packages in high volume production, while achieving higher device reliability.

In a further aspect, the present invention relates to a method for manufacturing such a sensor package, as defined in the preamble above. The method further comprises applying electrically conductive glue (or adhesive) to one or more of the plurality of lead frame members, positioning contact terminal parts of the first sensor element on the first side surface of the substrate against the electrically conductive glue on the one or more of the plurality of lead frame members, and moulding the package body at least in part around the substrate and the plurality of lead frame members and providing an aperture in the package body exposing at least in part a sensitive surface which is part of the first sensor element.

By applying such a method wherein the sensor package is provided with simplified internal electrical connections using a conductive glue or adhesive (which can be easily applied in liquid form), a reliable and cost-effective manufacturing method is provided. The sensor package according to the present invention embodiments further facilitates the manufacturing process such that overall complexity and cost of manufacturing is reduced. The present invention enables to protect the sensors and the supporting electronics to operate in a harsh environment such as an environment including corrosive gases and/or fluids, or an environment with a varying temperature.

SHORT DESCRIPTION OF DRAWINGS

The present invention will be discussed in more detail below, with reference to the attached drawings.

DESCRIPTION OF EMBODIMENTS

In many applications, sensors are being used for measuring a myriad of parameters which require exposure of a sensitive surface to an environment. It would be advantageous if a sensor can be made available in a sensor package which is similar to the well-known integrated circuit packaging technologies. This would allow cost-effective manufacturing and better integration in further electronics devices.

Figure 1B:
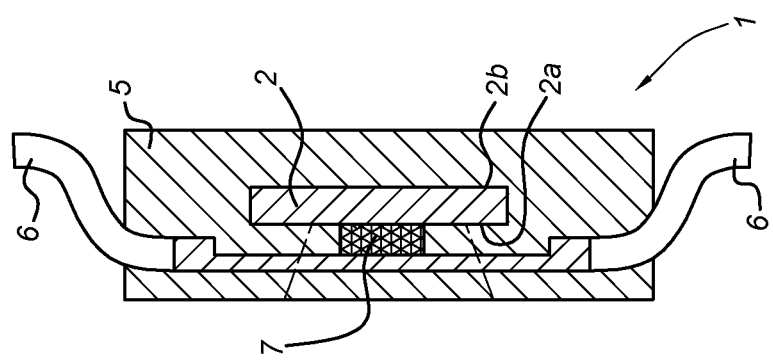
FIG. 1B shows a cross sectional view of the sensor package shown in FIG. 1A along the line IB-IB.
Figure 1A:
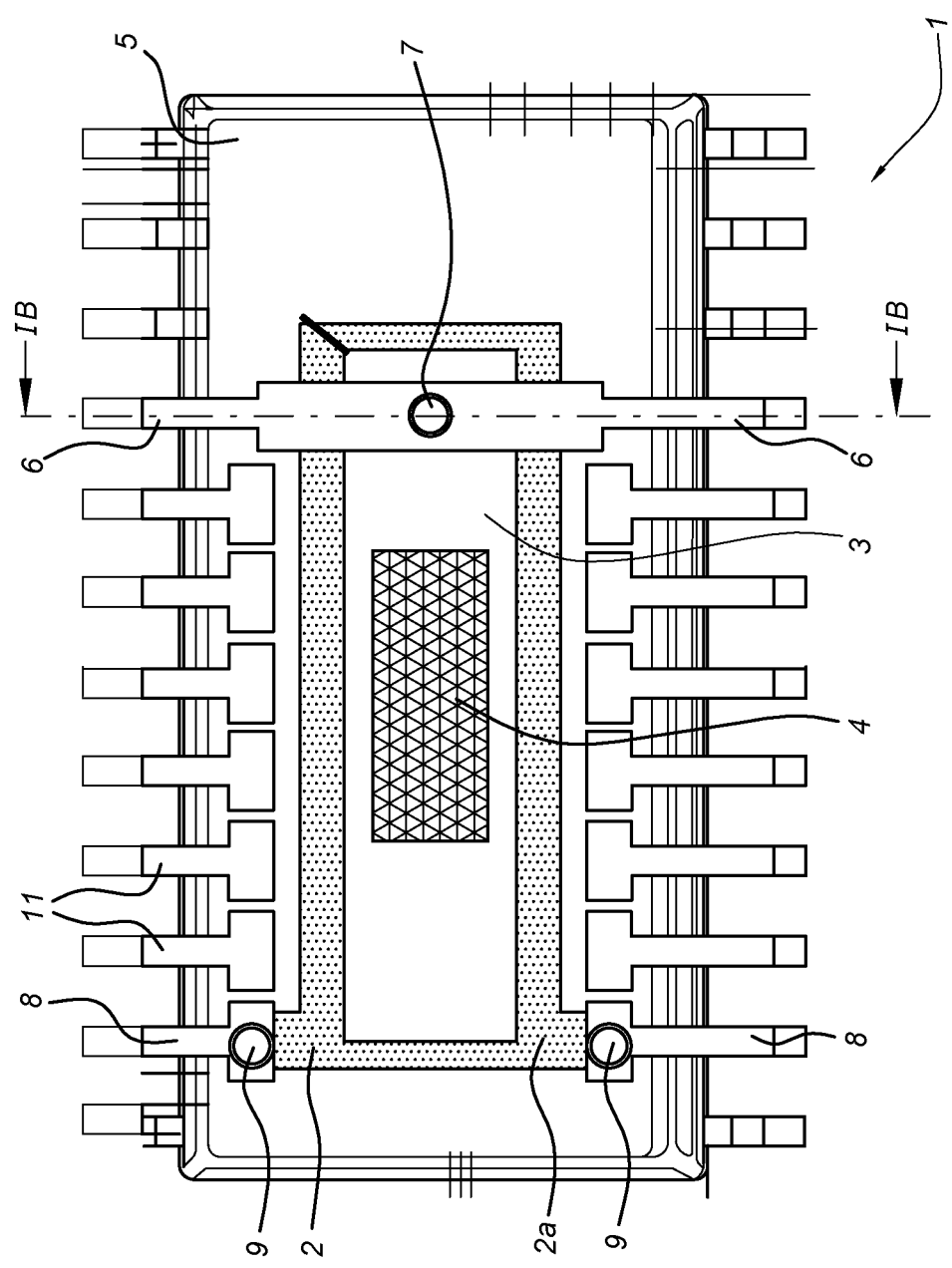
FIG. 1A shows a two dimensional top view of a sensor package 1 with a first sensor element on top according to an embodiment of the present invention.

FIG. 1A shows a top view of a sensor package 1 according to a first embodiment of the present invention. In this embodiment, the sensor package 1 comprises a package body 5 enclosing at least in part a substrate 2 and a plurality of lead frame members 6, 8, 11 (as a regular moulded package of e.g. an integrated circuit). In the embodiment shown, only the lead frame members indicated with reference numerals 6 and 8 are actually used as external contacts, while the further lead frame members 11 are not connected. The substrate 2 in this embodiment is arranged to be a first sensor element 3.

Electrical contact is provided between contact terminals of the sensor element 3 using an electrically conductive glue (or adhesive) connection 7, 9. In the embodiment shown, one of the sensor element terminals is connected to a bridging set of lead frame members 6 using an electrically conductive glue connection 7, and the other one of the sensor element terminals is connected to two lead frame members 8 using an electrically conductive glue connection 9. In general, any substrate 2 being arranged to act as a first sensor element 3 can be accommodated in the package body 5, and one, two or even more of the sensor element terminals can be connected to one, two or even more of the plurality of lead frame member 6, 8 for providing external connections. Suitable electrically conductive glue or adhesive compounds are readily available which can be applied easily on the lead frame members 6, 8. After bringing the lead frame member 6, 8 in contact with contact terminal parts of the first sensor element 3 with the electrically conductive glue connection 7, 9 in between, a strong and durable (electrical) connection is obtained (e.g. by evaporation of a solvent, or by applying a hardening radiation).

Thus, in a generic sense, the present invention embodiments relate to a sensor package comprising a package body 5 enclosing at least in part a substrate 2 and a plurality of lead frame members 6, 8, wherein the substrate 2 comprises a first sensor element 3 on a first surface 2a and wherein the package body 5 comprises an aperture 5a exposing a sensitive surface 4 of the first sensor element 3, and wherein the sensor package 1 further comprises an electrically conductive glue connection 7, 9 between contact terminals of the first sensor element 3 and one or more of the plurality of lead frame members 6, 8.

FIG. 1B shows a cross sectional view of the sensor package 1 shown in FIG. 1A along the line IB-IB. A cross sectional view is shown of the (bridged) lead frame member 6 within the packaged body 5. It comprises the lead frame 6 as the top structure which is connected to the first sensor element 3 by an electrically conductive glue 7. As shown in this cross sectional view, the substrate 2 comprises a first side surface 2a and a second side surface 2b. The lead frame comprising the plurality of lead frame members 6, 8 is designed to allow the glue based electrical connections 7, 9 by simply positioning the substrate 2 on its first side surface 2a onto predetermined quantities of glue 7, 9 on the proper aligned positions on the lead frames 6, 8, respectively. This cross sectional view clearly shows that the electrically conductive glue connection 7, 9 is provided on the first side surface 2a of the substrate 2.

In an exemplary embodiment the first sensor element 3 encapsulated within the sensor package 1 is a gas sensor, e.g. a hydrogen sensor. To implement a hydrogen sensor the substrate 2 is e.g. provided as a substrate with a titanium oxide layer 4, which is sensitized for detecting hydrogen ($H_2$) by adding platinum Pt (or alternatively palladium Pd). Other types of hydrogen sensors of a substrate type are also conceivable, e.g. based on a semiconductor oxide film such as tin oxide ($SnO_2$), silicon oxide ($SiO_2$) or titanium oxides (TiO or $TiO_2$), onto which one or more areas/layers of a noble metal acting as a catalyst, such as platinum or palladium, are applied (e.g. using a sputtering technique). In further alternatives, layers of catalyst material (e.g. palladium Pd) on a flexible or rigid substrate may be applied. More generically, the gas sensor in a further embodiment is a hydrogen gas sensor comprising a titanium oxide layer, wherein the electrically conductive glue connection 7, 9 is provided between terminal parts of the first sensor element 3 (i.e. one on the substrate 2 and one on the sensitive surface 4 part) and the one or more of the plurality of lead frame members 6, 8. The aperture 5a in the package body 5 allows to have a direct contact between the sensing area of the sensitive surface 4 and the gas to be sensed in the environment.

Figure 2:
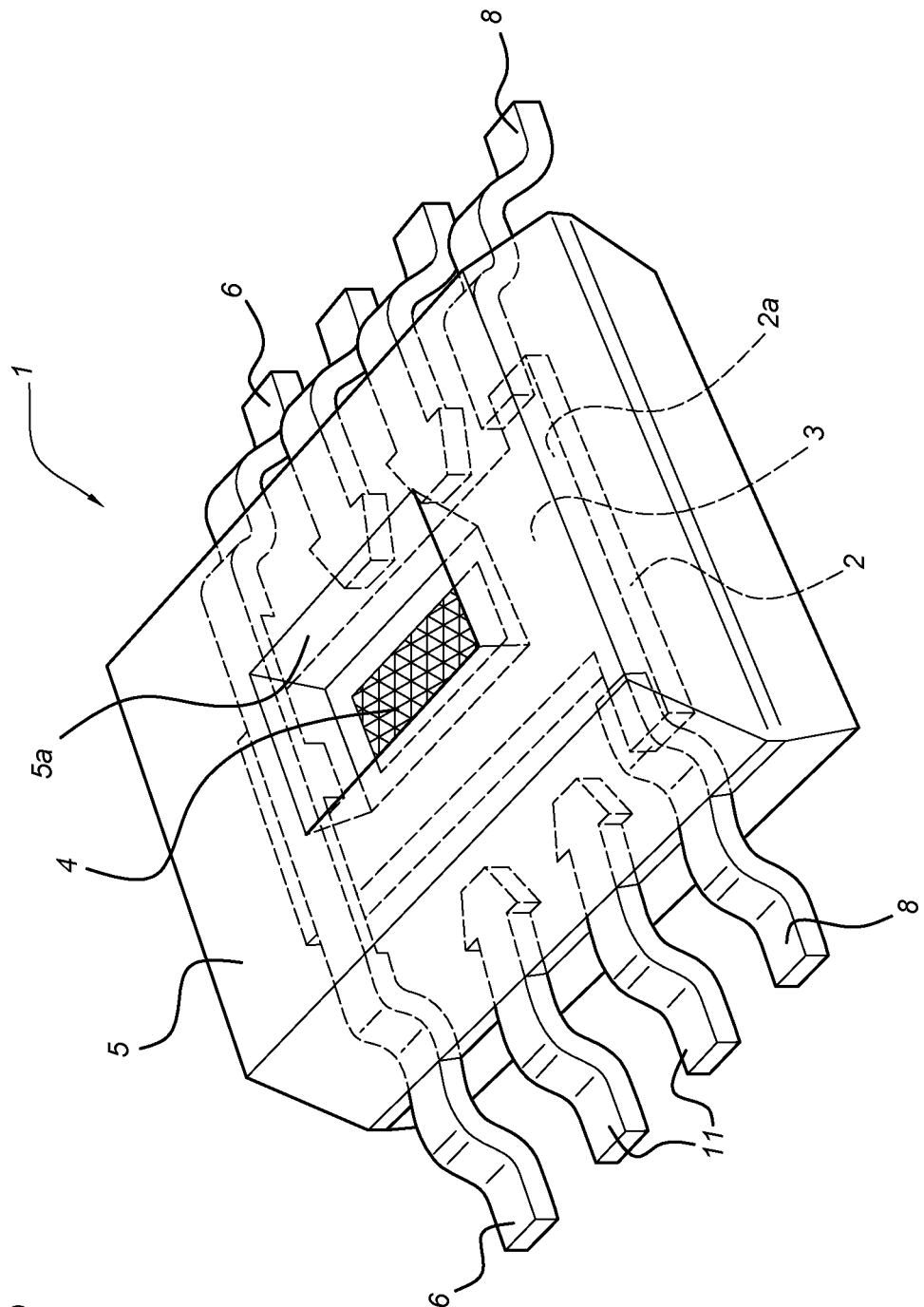
FIG. 2 shows a three dimensional view of a sensor package according to a further embodiment of the present invention.

FIG. 2 shows a three dimensional view of a sensor package 1 according to a further embodiment of the present invention. As shown, the package body 5 encloses at least in part the substrate 2 and the plurality of (connected) lead frame members 6, 8. The substrate 2 comprises a first side surface 2a provided with a first sensor element 3 (having a sensitive surface 4) and the package body 5 has an aperture 5a exposing at least in part the sensitive surface 4 of the first sensor element 3. The aperture 5a ensures a proper exposure of the sensitive surface 4 of the first sensor element 3 to the environment, while the IC like package body 5 and lead frame members 6, 8 allow for easy inclusion of the sensor package 1 in an electronic device.

Figure 3:
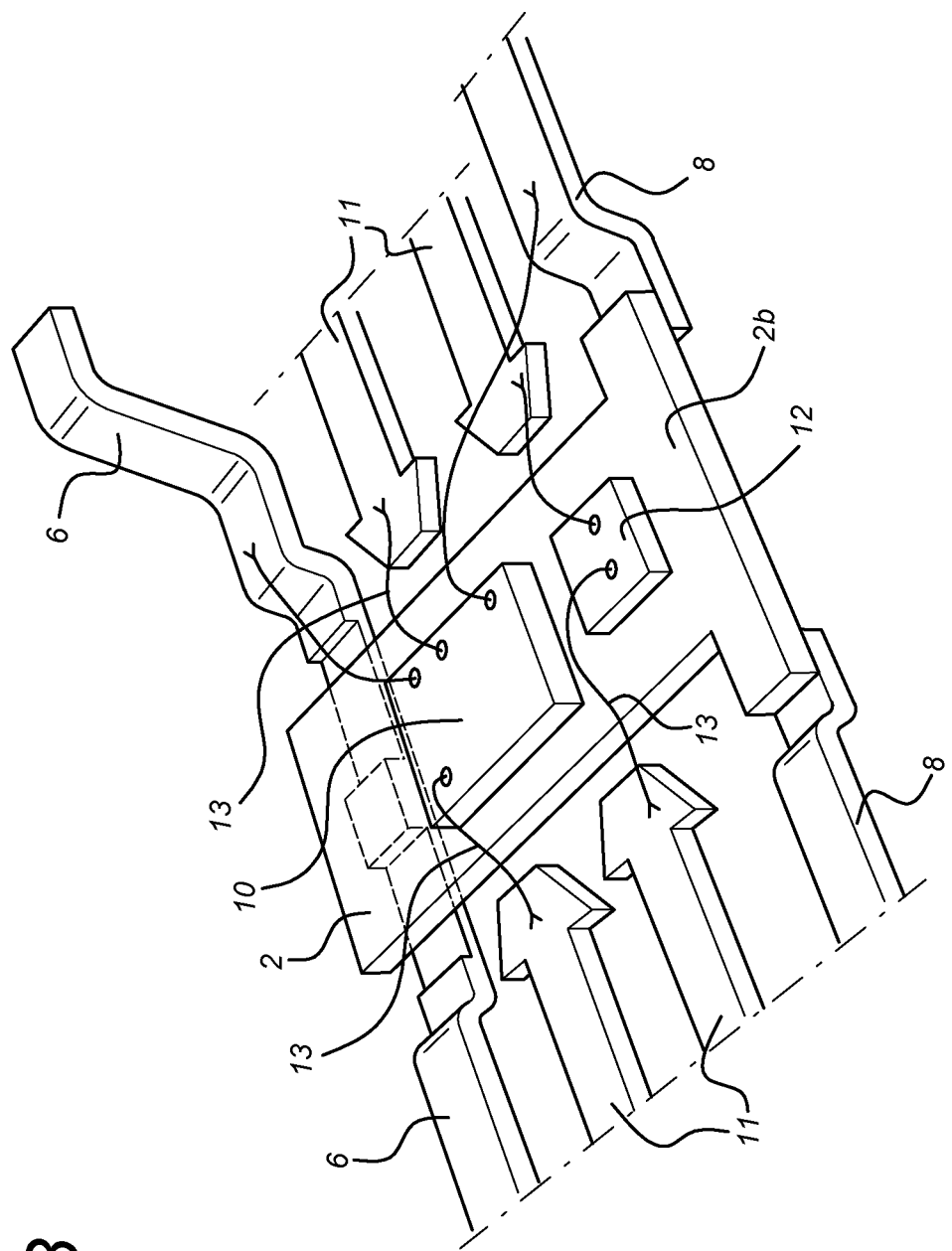
FIG. 3 shows a three dimensional view of a sensor package according to an even further embodiment of the present invention with additional components in the sensor package.

FIG. 3 shows a three dimensional view of a sensor package according to an even further embodiment of the present invention with additional components in the sensor package. The sensor package is provided with an integrated circuit 10 and/or a second sensor element 12 which are electrically connected to further ones of the plurality of lead frame members 11 via bonding wires 13. These bonding wires 13 are included in (and protected by) the package body 5 as in any normal integrated circuit package. The integrated circuit 10 and/or sensor element 12 are mechanically attached to the second surface side 2b of the substrate 2. In a generalization of this embodiment, the substrate 2 further comprises a second side surface 2b provided with one or more electronic components 10, 12, 14. As shown in the embodiment of FIG. 3, the one or more electronic components 10, 12, 14 are electrically connected by means of bonding wires 13 to further ones of the plurality of lead frame members 11.

In exemplary embodiments, the one or more electronic components 10, 12, 14 comprise, an integrated circuit 10, and/or a second sensor element 12, e.g. a temperature sensor. As shown in the embodiment of FIG. 3, the terminals of the second sensor element 12 are connected to further lead frame members 11 via bonding wires 13. Additionally or alternatively, bonding wires 13 may also be provided directly between second sensor element 12 and integrated circuit 10. The characteristic response of a gas sensor (or as an example a hydrogen sensor) as implemented in the first sensor element 3 is affected by variation in temperature, and this effect must be considered in a real life application of gas sensors. To overcome this limitation, the first sensing element 3 is accompanied by a second sensing element 12 in the form of a temperature sensor on the same substrate 2 (on its second side surface 2b). In this way it is possible to correct the measurement signal from the gas sensor (first sensing element 3) to obtain a reliably measured gas concentration under varying temperatures. As mentioned above, for electrical connection, the second sensor element 12 in this embodiment is wire bonded (using bonding wire 13) to further ones of the plurality of lead frame members 11.

Figure 4:
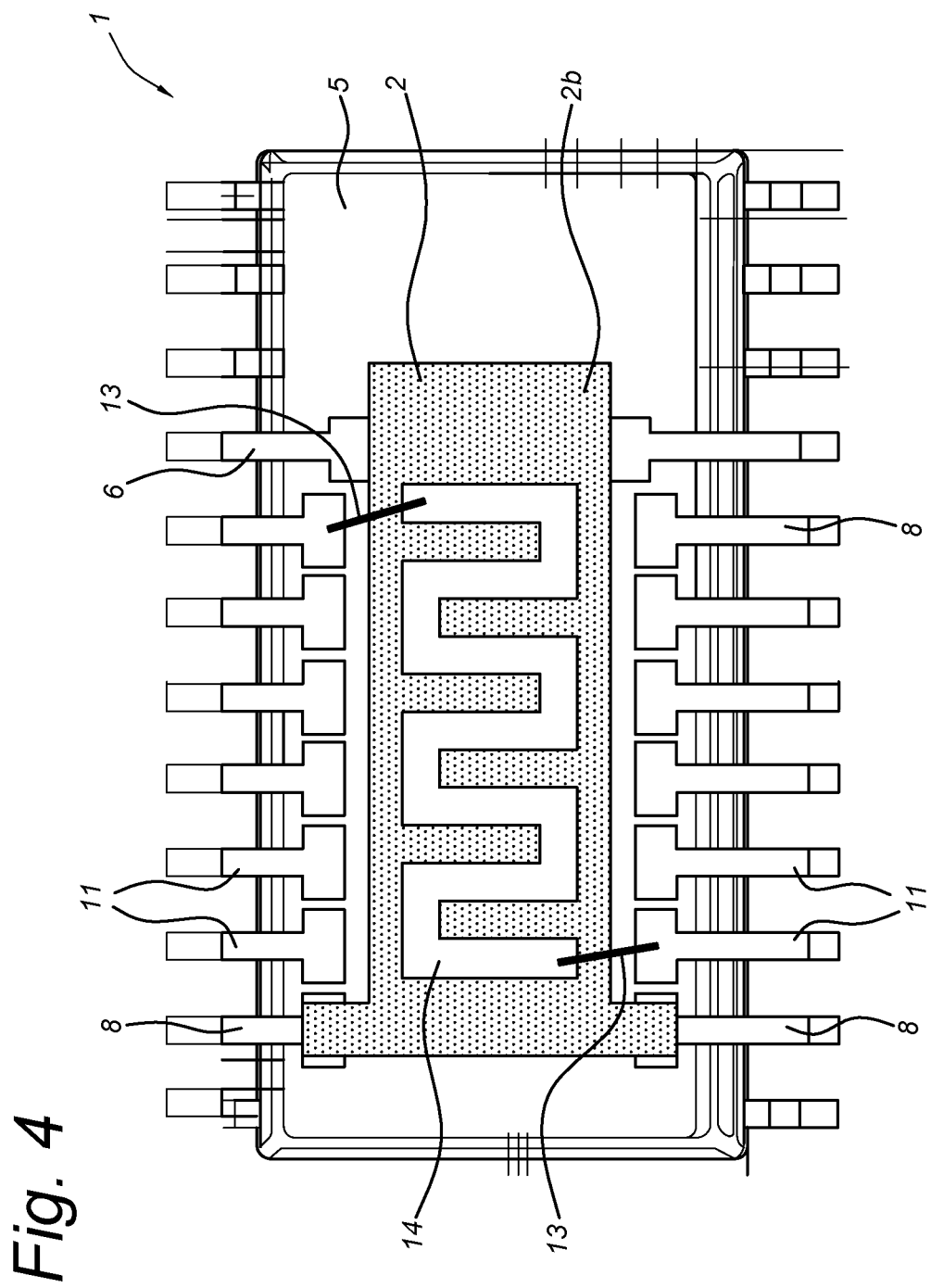
FIG. 4 shows a bottom view of a sensor package according to an even further embodiment of the present invention with a heater element.

FIG. 4 shows a (two dimensional) bottom view of a sensor package 1 according to an even further embodiment of the present invention with a heater element 14. The heater element 14 is provided directly onto the second side surface 2b of the substrate 2, e.g. as a thin film resistor element. The heater element 14 is electrically connected to two further ones of the plurality of lead frame members 11, again using bonding wires 13.

In a further aspect, the present invention also relates to a method of manufacturing a sensor package according to any one of the embodiments described above. The inventive method embodiments comprise providing a lead frame of electrically conductive material, the lead frame comprising a plurality of lead frame members 6, 8; applying electrically conductive glue to one or more of the plurality of lead frame members 6, 8; positioning contact terminal parts of the first sensor element 3 on the first side surface 2a of the substrate 2 against the electrically conductive glue on the one or more of the plurality of frame members 6, 8; and moulding the package body 5 at least in part around the substrate 2 and the plurality of lead frame members 6, 8 and providing an aperture 5a in the package body 5 exposing at least in part a sensitive surface part 4 of the first sensor element 3. As in a normal process for manufacturing an integrated circuit package, also in this process for manufacturing a sensor package, the method may further comprise trimming a portion of the lead frame that extends outside the package body 5 to provide the sensor package 1 with a plurality of external electrical contacts. For the embodiments wherein further electronic components 10, 12, 14 are provided on the second side surface 2b of the substrate, the method in a further embodiment further comprises providing one or more electronic components 10, 12, 14 on a second side surface 2b of the substrate 2; and wire bonding the one or more electronic components 10, 12, 14 to further ones of the plurality of lead frame members 11.

The above described exemplary embodiments may be summarized in the following interdependent and numbered embodiment descriptions:

The present invention has been described above with reference to a number of exemplary embodiments as shown in the drawings. Modifications and alternative implementations of some parts or elements are possible, and are included in the scope of protection as defined in the appended claims.

The invention claimed is:

1. An integrated circuit sensor package comprising
a package body moulded at least in part around a substrate and a plurality of lead frame members,
wherein the substrate comprises a first sensor element on a first side surface of the substrate and wherein the package body comprises an aperture exposing a sensitive surface of the first sensor element, wherein the aperture is arranged to allow direct contact between a sensing area of the sensitive surface and an environment; and
wherein the integrated circuit sensor package further comprises an electrically conductive glue connection between contact terminals of the first sensor element and one or more of the plurality of lead frame members, wherein the electrically conductive glue connection is provided on the first side surface of the substrate, and wherein the substrate further comprises a second side surface opposite the first side surface.

2. The integrated circuit sensor package according to claim 1, wherein the the first side surface of the substrate is an upper side.

3. The integrated circuit sensor package according to claim 1, wherein the first sensor element is a gas sensor.

4. The integrated circuit sensor package according to claim 3, wherein the gas sensor is a hydrogen gas sensor comprising a titanium oxide layer, wherein the electrically conductive glue connection is provided between terminal parts of the first sensor element and the one or more of the plurality of lead frame members.

5. The integrated circuit sensor package according to claim 1, wherein the second side surface is provided with one or more electronic components.

6. The integrated circuit sensor package according to claim 5, wherein the one or more electronic components are electrically connected by means of bonding wires to further ones of the plurality of lead frame members.

7. The integrated circuit sensor package according to claim 5, wherein the one or more electronic components comprises a second sensor element.

8. The integrated circuit sensor package according to claim 5, wherein the one or more electronic components comprises an integrated circuit.

9. The integrated circuit sensor package according to claim 5, wherein the one or more electronic components comprises a thin film heater element on the second side surface.

10. A method of manufacturing an integrated circuit sensor package, the method comprising:
providing a lead frame of electrically conductive material, the lead frame comprising a plurality of lead frame members;
applying electrically conductive glue to one or more of the plurality of lead frame members;
positioning contact terminal parts of the first sensor element on the first side surface of the substrate against the electrically conductive glue on the one or more of the plurality of lead frame members, wherein the electrically conductive glue is provided on the first side surface of the substrate, and wherein the substrate further comprises a second side surface opposite the first side surface; and
moulding the package body at least in part around the substrate and the plurality of lead frame members and providing an aperture in the package body exposing at least in part a sensitive surface of the first sensor element, wherein the aperture is arranged to allow direct contact between a sensing area of the sensitive surface and an environment.

11. The method od according to claim 10, further comprising trimming a portion of the lead frame that extends outside the package body to provide the sensor package with a plurality of external electrical contacts.

12. The method according to claim 10, further comprising providing one or more electronic components on the second side surface of the substrate;
wire bonding the one or more electronic components to further ones of the plurality of lead frame members.

13. The integrated circuit sensor package according to claim 7, wherein the second sensor element is a temperature sensor.

14. The integrated circuit sensor package according to claim 1, wherein an environment is an environment outside the integrated circuit sensor package.

* * * * *